United States Patent
Steffen

[11] 3,963,739
[45] June 15, 1976

[54] 3-AMINO-4,5,6-TRICHLORO-7-NITRILOINDAZOLES

[75] Inventor: Klaus-Dieter Steffen, Troisdorf-Oberlar, Germany

[73] Assignee: Dynamit Nobel Aktiengesellschaft, Troisdorf, Germany

[22] Filed: Aug. 4, 1975

[21] Appl. No.: 601,950

Related U.S. Application Data

[63] Continuation of Ser. No. 398,629, Sept. 19, 1973, abandoned.

[30] Foreign Application Priority Data

Sept. 30, 1972  Germany............................ 2248175

[52] U.S. Cl............................................ 260/310 C
[51] Int. Cl.²......................................... C07D 231/56
[58] Field of Search................................. 260/310 C

[56] References Cited
OTHER PUBLICATIONS

Beck et al. "Liebigs Ann. Chem." 716, pp. 47–60, (1968).

*Primary Examiner*—Donald B. Moyer
*Attorney, Agent, or Firm*—Burgess, Dinklage & Sprung

[57] ABSTRACT

A compound having the formula

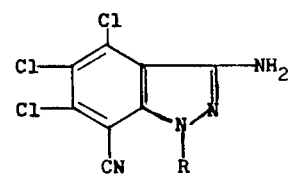

wherein R is hydrogen, a $C_{1-6}$ alkyl, a $C_{1-6}$ chloroalkyl, a phenyl or an alkyl-substituted phenyl radical, a process for preparing such compound by contacting tetrachlorisophthalic acid dinitrile with hydrazine or a hydrazine derivative of the formula $H_2N-NHR$ in which R has the previously ascribed significance.

3 Claims, No Drawings

3-AMINO-4,5,6-TRICHLORO-7-NITRILOINDAZOLES

This is a continuation of application Ser. No. 398,629, filed Sept. 19, 1973, now abandoned.

BACKGROUND OF THE INVENTION

1. Field of the Invention

This invention relates to the preparation of 3-amino-4,5,6-trichloro-7-nitriloindazoles and a method of preparing the same. This invention is also directed to the preparation of 3-amino-4,5,6-trichloro-7-nitriloindazoles which are substituted on one of the nitrogen atoms of the indazole moiety. The present invention is directed to the method of preparing such compounds.

2. Discussion of the Prior Art 3-aminoindazoles and $N^1$ derivatives thereof are known, which are substituted in the 4th or 5th position by chlorine, bromine or the trifluormethyl group. These compounds may be prepared by the reaction of an o-halobenzonitrile with hydrazine or a hydrazine derivative, the reaction temperature being preferably above 45°C and hydrochloric acid being required as a catalyst for the cyclization reaction. These compounds are used directly or in the form of their salts as pharmaceuticals.

SUMMARY OF THE INVENTION

Broadly, this invention contemplates a compound of the formula

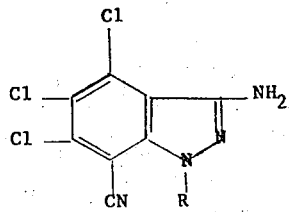

wherein R represents hydrogen, $C_{1-6}$ alkyl, $C_{1-6}$ chloralkyl, phenyl or alkyl-substituted phenyl radical.

The present invention also contemplates structural isomers of such compounds having the formula

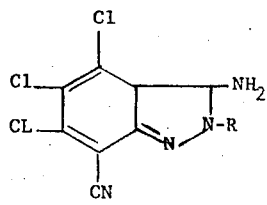

in which R has the previously assigned significance. These compounds are prepared in accordance with the invention but their formula is less favored for reasons relating to the kinetics of the reaction from those having the first formula set forth above.

The compounds of the invention are prepared by contacting tetrachlorisophthalic acid dinitrile with a hydrazine compound of the formula

in which R is hydrogen, a $C_{1-6}$ alkyl, a $C_{1-6}$ chloralkyl, a phenyl or an alkyl-substituted phenyl radical. If R is an alkyl-substituted phenyl radical, the phenyl group can be substituted by more than one alkyl group. Generally, there are between 1 and 6 carbon atoms in the alkyl group substituted on the phenyl radical. Groups such as tolyl groups and xylyl groups are contemplated. The reaction according to the present invention can be carried out when R represents other radicals such as, for example, polynuclear phenols or long chain alkyl groups which can by halogen-substituted. Thus R can represent a halo phenyl group or a hydroxy phenyl group. Other substituents which can be present on the organic radical R include —$CH_2$—$CH_2OH$ and —CHOH; when the reaction is carried out with the last mentioned compounds, the resulting indazole contains more impurities than the products obtained with hydrazine derivatives with completely inert substituent. These groups can contain reactive groups capable of entering into an analogous reaction competitive with that of the hydrazine compound. This is so even when the active substituent on the R radical reacts more rapidly than that of the hydrazine itself.

DISCUSSION OF SPECIFIC EMBODIMENTS

The compounds of the present invention can be prepared at ambient temperatures. For instance, the reaction can take place with surprising success and with good rapidity at temperatures between 10° and 50°C, resulting in yields of better than 90% by weight based upon the limiting reactant, without the use of a catalyst if the reaction is performed in a suitable solvent. The use of low temperatures is at least in part required on account of the presence of two nitrilo groups in one of the starting reactants. Accordingly, the reaction is carried out at the lowest possible temperature so that only one of the two nitrilo groups reacts with the hydrazine compound.

As indicated above, the process can be beneficially conducted in the presence of the solvent. Preferably, the solvent employed for the reaction is one in which the product is sparingly soluble or is insoluble.

Suitable solvents are those compounds in which the starting compounds are easily soluble and in which the end products obtained are difficultly soluble at room temperature. In general, dioxane is especially suitable, either as a pure isomer or as an isomer mixture. In special cases the reaction can also be performed in low alcohols, acetone or acetonitrile as the solvent.

Generally speaking, there are between 1 and 3 moles, preferably between 1 and 2 moles of hydrazine compound per mole of tetrachloroisophthalic acid dinitrile. The reaction is normally carried out at atmospheric pressure although pressures as high as 10 atmospheres can be employed.

The hydrochloric acid released in the reaction is preferably intercepted with excess hydrazine. It can also be neutralized, however, by the addition of other bases such as soda or triethylamine, for example.

The end product crystallizes out of the reaction mixture and after washing with water it is already very pure. The yields, when dioxane is used as the solvent, are above 90% and are therefore higher than in similar processes for the preparation halogen-substituted aminoindazoles in which the reaction is performed at temperatures of 150°C with dimethylformamide as the solvent.

As a result of the reactive nitrilo group, which can be saponified or hydrogenated, the new compound can be used as starting products for other pharmaceutical of complex construction which have effects to a greater or lesser degree on the central nervous system and which can be used especially as muscular relaxants, analgesics, antipyretics or as mild tranquilizers.

The amino halo indazoles prepared by the process of the invention can be used as muscle relaxants, analgesics, anitpyretics or as mild tranquilizers in accordance with the mode of application disclosed in U.S. Pat. No. 3,133,081 to Lafferty et al. The 3-aminoindazole derivatives of this invention could therefore be employed in pharmaceutical form in admixture with the pharmaceutical carrier. The pharmaceutical carrier may be either a solid or a liquid. Exemplary of solid carriers are lactose, magnesium stearate, terra alba, sucrose, talc, stearic acid, gelatine, agar, pectin, and acacia. Exemplary of liquid carriers are peanut oil, olive oil, sesame oil, and water. A wide variety of pharmaceutical forms can be used. Thus, if a solid carrier is used, the preparation can be in the form of a tablet, pharmaceutical powder, a hard gelatine capsule, a troche or a lozenge. If a liquid carrier is used, the preparation can be in the form of a soft gelatine capsule, or may be placed in an ampoule or in a liquid suspension. A dosage unit for internal administration conprises from about 25 mg. to 350 mg., preferably from about 50 to about 200 mg. of active ingredient. The administration may be carried out interiorly or orally. Advantageously, equal doses would be administered from one to four times daily.

The new compounds are largely yellow-colored and have melting points above 200°C, often beginning to sublimate. With inorganic and organic acids they form salts, such as the corresponding hydrochlorides or acetates, for example.

In order to more fully illustrate the nature of the invention and the manner of practising the same, the following examples are set forth:

EXAMPLE 1

In a three-necked flask provided with stirrer, condenser and dropping funnel 13.29 g of tetrachlorisophthalicaciddinitrile (0.05 mole) is dissolved in 170 ml of dioxane with heating at about 60°C. To this solution, cooled to room temperature, a solution of 5.5 g of hydrazine hydrate (100% solution, 0.11 mole) is added drop by drop. The reaction is slightly exothermic. The mixture was stirred at room temperature for about 22 hours and then the yellow precipitate was filtered out, washed with dioxane and water, and dried. 12.37 g (= 94.5% of the theory) was obtained.

The crude product was recrystallized from about 9 liters of methanol; 9.41 g (= 72.0% of the theory) was then obtained of a very pure product with a melting point of 339 to 344°C (determined in a sealed capillary). At the melting point a slight decomposition occurred Crude formula: $C_8H_3Cl_3N_4$, molecular weight 261.50.

Elemental analysis: Calculated: C 36.74, H 1.16, Cl 40.67, N 21.43; Found: C 36.35, H 1.20, Cl 39.67, N 21.35.

The product was 3-amino-4,5,6-trichloro-7-nitriloindazole

The molecular peak determined by mass spectrometry is at 261.

Without heating, the compound is soluble in sulfuric acid, trifluoracetic acid, tetrahydrofuran, dimethylsulfoxide, dimethylformamide, dimethylacetamide and N-methylpyrrolidone, among others, and insoluble in dioxane, low aliphatic alcohols and ether, for example.

With heating, it is partially soluble in methyl alcohol and ethyl alcohol, dioxane, o-dichlorbenzene and glacial acetic acid, for example.

EXAMPLE 2

In the manner described in Example 1, 13.29 g of tetrachlorisophthalicaciddinitrile (0.05 mole) was brought to reaction in a dioxane solution with 11.9 g of phenylhydrazine (0.11 mole). After 22 hours reaction time the yellow precipitate was filtered out, washed with dioxane and water, and dried.

Crude yield: 16.07 g (95.20% of the theory).

The product was recrystallized from tetrahydrofuran, dioxane or acetonitrile. Melting point 290° to 296°C (determined in sealed capillaries). Crude formula: $C_{14}H_7Cl_3N_4$, molecular weight: 337.59.

Elemental analysis: Calculated: C 49.81, H 2.09, Cl 31.51, N 16.60; Found: C 49.87, H 2.00, Cl 31.15, N 16.62.

The product was 3-amino-4,5,6-trichloro-7-nitrilo-N′-phenylindazole.

On the basis of differential thermoanalysis this compound has a melting point of 294°C and the following weight losses (rate of heating 8° per minute): 1%: 304°C, 5%: 331°C, 10%: 345°C, 20%: 378°C.

Without heating, the product is soluble in dimethylformamide, dimethylacetamide, tetrahydrofuran, etc. With heating, it is soluble in nearly all available solvents. Suitable for crystallization and recrystallization are acetonitrile, dioxane, methanol, toluene.

EXAMPLE 3

In the manner described in Example 1, 13.29 g of tetrachlorisophthalicaciddinitrile (0.05 mole) was brought to reaction in a dioxane solution with 5.1 g of methylhydrazine (0.11 mole). The yellow crystalline mass that precipitated was filtered out after about 20 hours of reaction time, washed with dioxane and water, and dried.

Yield: 12.77 g (92.8% of the theory).

Recrystallization was performed from acetonitrile or acetone. Melting point 275° to 281°C.

Crude formula: $C_9H_5Cl_3N_4$, molecular weight: 275.53.

Elemental analysis: Calculated: C 39.23, H 1.83, Cl 38.60, N 20.33; Found: C 39.59, H 2.16, Cl 37.66, N 20.20.

The product was 3-amino-4,5,6-trichloro-7-nitrilo-N′-methylindazole.

On the basis of differential thermoanalysis (heating rate 8°/min) the substance has a transformation point at 256°C, a melting point of 281°C and the following weight losses: 1%: 256°C, 5%: 304°C, 10%: 328°C, 20%: 350°C.

With heating, the compound is soluble in dimethylformamide, acetone, acetonitrile, chloroform, etc., whereas it is poorly soluble in these solvents at room temperature. Acetone and acetonitrile are suitable for recrystallization.

It will be realized from the above disclosure that the chlorine atoms on the phenyl group of the indazole compounds of the present invention can be removed and another halogen can be substituted in lieu thereof. Thus the present invention contemplates a compound having the formula

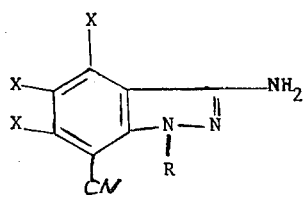

wherein each X is independently selected from the group consisting of chlorine, bromine, and R represents hydrogen, a $C_{1-6}$ alkyl group, a $C_{1-6}$ chloralkyl group, a phenyl group, an alkyl substituted phenyl group wherein the alkyl group has between 1 and 6 carbon atoms, a moiety of a polynuclear phenol or a substituted alkyl group having 1 to 18 carbon atoms, especially an alkyl substituted by a halogen atom.

What is claimed is:

1. In a method of preparing a 3-amino-4,5,6-trichloro-7-nitriloindazole of the general formula

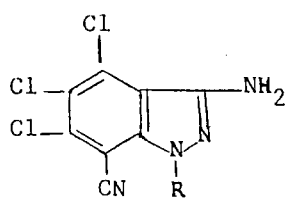

wherein R represents hydrogen, alkyl of from 1 to 6 carbon atoms, chloroalkyl of from 1 to 6 carbon atoms, phenyl or alkyl-substituted phenyl, the alkyl portion of which is an alkyl of from 1 to 6 carbon atoms by contacting a tetrachloroisophthalicaciddinitrile having the formula

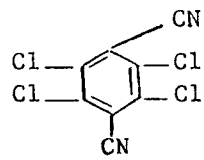

with a hydrazine compound of the formula $H_2N-NHR$ the improvement which comprises carrying out said process at a temperature between 10° and 50°C in the presence of a solvent for the reaction mixture, which solvent is selected from the group consisting of dioxane, methyl alcohol, ethyl alcohol, o-dichlorobenzene, ethyl ether and toluene and thereafter recovering a 3-amino-4,5,6-trichloro-7-nitriloindazole.

2. Method according to claim 1 wherein the reaction is conducted in the presence of dioxane solvent.

3. Method according to claim 1 wherein said 3-amino-4,5,6-trichloro-7-nitriloindazole is removed from the reaction mixture by initially precipitating the same by employing a solvent for the reaction in which the product is only poorly soluble.

* * * * *

UNITED STATES PATENT AND TRADEMARK OFFICE
CERTIFICATE OF CORRECTION

PATENT NO. : 3,963,739
DATED : June 15, 1976
INVENTOR(S) : Klaus-Dieter Steffen

It is certified that error appears in the above-identified patent and that said Letters Patent are hereby corrected as shown below:

Column 1, lines 46-55, the drawing shown should be deleted and the following drawing substituted therefor:

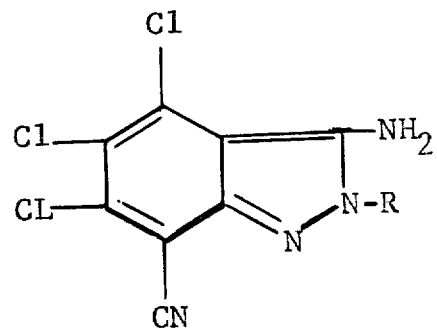

Signed and Sealed this

Twenty-first Day of September 1976

[SEAL]

Attest:

RUTH C. MASON
Attesting Officer

C. MARSHALL DANN
Commissioner of Patents and Trademarks